United States Patent
Peyman

(10) Patent No.: US 6,296,867 B1
(45) Date of Patent: Oct. 2, 2001

(54) THERAPEUTIC CONTACT LENS COMPRISING LIVING CELLS WITHIN A MATRIX

(76) Inventor: Gholam A. Peyman, 8654 Portchartrain Blvd., New Orleans, LA (US) 70124

(*) Notice: Subject to any disclaimer, the term of this patent is extended or adjusted under 35 U.S.C. 154(b) by 0 days.

(21) Appl. No.: 09/560,810

(22) Filed: Apr. 28, 2000

(51) Int. Cl.[7] .............................. A61K 9/00; A61K 9/14; A01N 1/00; C12N 1/00; C08G 63/48
(52) U.S. Cl. ..................... 424/429; 424/484; 424/486; 424/488; 435/1; 525/64; 525/200; 525/932; 525/937
(58) Field of Search ..................... 424/429, 486, 424/488; 525/64, 937, 200; 435/1

(56) References Cited

U.S. PATENT DOCUMENTS

| | | |
|---|---|---|
| 4,231,905 | 11/1980 | Neefe . |
| 4,646,720 | 3/1987 | Peyman et al. . |
| 4,676,790 | 6/1987 | Kern . |
| 4,840,175 | 6/1989 | Peyman . |
| 5,030,230 | 7/1991 | White . |
| 5,133,708 * | 7/1992 | Smith . |
| 5,157,093 | 10/1992 | Harisiades et al. . |
| 5,281,294 * | 1/1994 | Freeman et al. . |
| 5,770,229 * | 6/1998 | Tanihara et al. . |
| 5,843,743 | 12/1998 | Hubbell et al. . |
| 5,910,537 * | 6/1999 | Feingold et al. . |

FOREIGN PATENT DOCUMENTS

| | | |
|---|---|---|
| 6616172A * | 5/1967 | (NL) . |
| WO 98/31316 * | 7/1998 | (WO) . |

* cited by examiner

*Primary Examiner*—Jon P. Weber
*Assistant Examiner*—Michele Flood
(74) *Attorney, Agent, or Firm*—Roylance, Abrams, Berdo & Goodman, L.L.P.

(57) ABSTRACT

A theraputic lens for removable placement onto a surface of a cornea of an eye, and methods for making and using the same. The lens has a first surface adapted for exposure to light and a second surface adapted to contact the surface of the cornea. The first and second surfaces define a portion which is adapted to allow visible light to pass and includes living cells forming at least part of the portion. In addition, the curvature of the lens can be modified by positioning the contact lens onto the surface of the cornea of the eye, and directing a beam of radiant energy onto the second surface in a predetermined pattern to ablate a section of the portion to form a lens of a desired shape.

24 Claims, 5 Drawing Sheets

THERAPEUTIC CONTACT LENS COMPRISING LIVING CELLS WITHIN A MATRIX

FIELD OF THE INVENTION

The present invention relates to a therapeutic contact lens and a method for manufacturing and using the same. More particularly, the present invention relates to a therapeutic contact lens that can be formed from living cells, and which provides relief to the eye and promotes healing. In addition, the lens can be shaped to have refractive properties while the lens is either positioned on the eye or before the lens is positioned on the eye.

DESCRIPTION OF THE RELATED ART

Conventional therapeutic lenses are well known in the optical art. Generally, therapeutic contact lenses are formed from a synthetic material such as silicon, hydrogel or polymetylmetacrylate. This type of lens is often a soft contact lens that possesses high oxygen permeability. The lens may be coated with active biological molecules and used as a drug delivery device. In addition, the lens may be shaped to refract light prior to placement onto the surface of the cornea of the eye.

However, these types of contact lenses, which are generally formed entirely from a synthetic material, usually irritate the eye and cause discomfort to the wearer of the lens, even if the lens is coated with lubricant. For example, the lubricant may wear off the lens or the individual's eye may be hypersensitive. In general, it is not uncommon for the wearer of the contact lens to be aware that the lens is positioned on the cornea or even experience a stinging sensation in the eye having the contact lens. Many improvements have sought to overcome this problem and increase the comfort level of the wearer of the contact lens. These improvements have led to the introduction of the soft contact lens and breathable contact lenses that have a high water content and induce the eye to coat the lens with water released from tear ducts. Examples of these types of lenses are disclosed in U.S. Pat. No. 5,843,743 to Hubbell et al.; U.S. Pat. No. 5,157,093 to Harisiades et al.; and U.S. Pat. No. 4,231,905 to Neefe, the entire contents of each are incorporated herein by reference.

Other lenses have attempted to correct vision disorders using biological tissue, such as corneal tissue, as a lens that is surgically implanted in the eye. These types of lenses use the biological tissue to facilitate integration as a corneal inlay. This procedure requires that part of the cornea be removed and a transparent lens be attached to the remaining portion of the cornea. Corneal tissue is used in an attempt to create a matrix between the existing live cornea and the implanted lens. However, the corneal tissue is preserved and is not living. Also, unlike a contact lens which may be easily removed from and placed onto the cornea by the wearer of the lens, the corneal inlay is a permanent, surgically implanted device that is not easily removed. Examples of these types of inlays are disclosed in U.S. Pat. No. 5,030,230 to White; and U.S. Pat. No. 4,676,790 to Kern, the entire contents of each are incorporated herein by reference.

In addition, methods for permenatly correcting vision disorders have included surgicaly attaching donor cornea to a host cornea. In such methods, a synthetic lens is positioned on the host cornea and held in place by the donor cornea surgically attached using sutures. However, the donor cornea is generally from an eye bank and is not grown in a culture. Additionally, the donor cornea is not a conact lens. It is surgically attached to the eye and may not be removed without undergoing a difficult surgical procedure. An example of this procedure is disclosed in U.S. Pat. No. 4,646,720 to Peyman, the entire contents of which is incorporated herein by reference.

Conventional contact lenses are also shaped to have refractive properties in a variety of ways. Generally a lens can be machined and polished to have a certain refractive measurement. The machining method is similar to the method in which lenses for glasses may be produced for vision correction. Typically a lens having no refractive power is machined to form a refractive lens having, for example, a concave or a convex shape. The lens is then polished to have a smooth exterior surface. The inherent problem with this type of lens is that each individual eye is different, thus making each individual vision problem different. The lenses are manufactured prior to placement on the eye, and machined and polished to the specifications that are measured and calculated from the eye. This procedure results in measurements not specifically tailored to the eye and sometimes requiring trial of several different lenses until the proper corrective or refractive properties produce the best-corrected vision.

More exact methods for connecting vision are known in the prior art of Lasik or photo refractive kratectomy. In these procedures, an excimer laser is directed at the cornea of an eye and a portion of the cornea is ablated in a predetermined pattern that personally corrects an individual's eyesight. Using wavefront technology, the refractive power of the eye is measured and the information is then fed to program that determines what portion of the eye needs to be ablated to achieve the best corrected vision. It is not uncommon in these procedures to have eyesight that results in better than 20/20 vision. An example of this procedure is disclosed in U.S. Pat. No. 4,840,175 to Peyman, the entire contents of which is incorporated herein by reference. Although this procedure is adequate for permanently correcting the vision of an eye, it has not been used to change the optical refractive power of a contact lens.

Thus, there is a continuing need to improve the interaction between the eye and a contact lens placed therein, and to improve the refractive properties of the contact lens to be more tailored to a specific problem of each wearer.

SUMMARY

Accordingly, it is an object of the present invention to provide a contact lens for removable placement on a surface of a cornea of an eye that improves the interaction between the eye and the lens, thus reducing irritation and increasing the comfort level.

Another object of the present invention is to provide a contact lens, for removable placement on a surface of a cornea of an eye, that can be shaped to have refractive properties while on the surface of the cornea.

Yet another object of the present invention is to provide a contact lens for removable placement on a surface of a cornea of an eye that is a custom or personal contact lens with substantially perfect corrective properties.

The foregoing objects are basically obtained by providing a therapeutic contact lens comprising living cells that enhances the healing process for removable placement onto a surface of a cornea and/or a conjunctiva of an eye. Specifically, the lens includes a first surface adapted for exposure to light and a second surface adapted to contact the surface of the cornea, with the first and second surfaces defining a portion therebetween including living cells and being adapted to allow visible light to pass therethrough.

Additionally, the foregoing objects are obtained by providing a method for modifying the curvature of a contact lens, comprising the steps of positioning the contact lens on a surface of a cornea of an eye, and modifying the contact lens using energy to ablate a portion of the contact lens while the contact lens is on the surface of the cornea.

Other objects, advantages and salient features of the invention will become apparent from the following detailed description, which, taken in conjunction with the annexed drawings, disclose preferred embodiments of the invention.

BRIEF DESCRIPTION OF THE DRAWINGS

Referring to the drawings which form a part of this disclosure.

DETAILED DESCRIPTION OF THE PREFERRED EMBODIMENT

Figure 1:
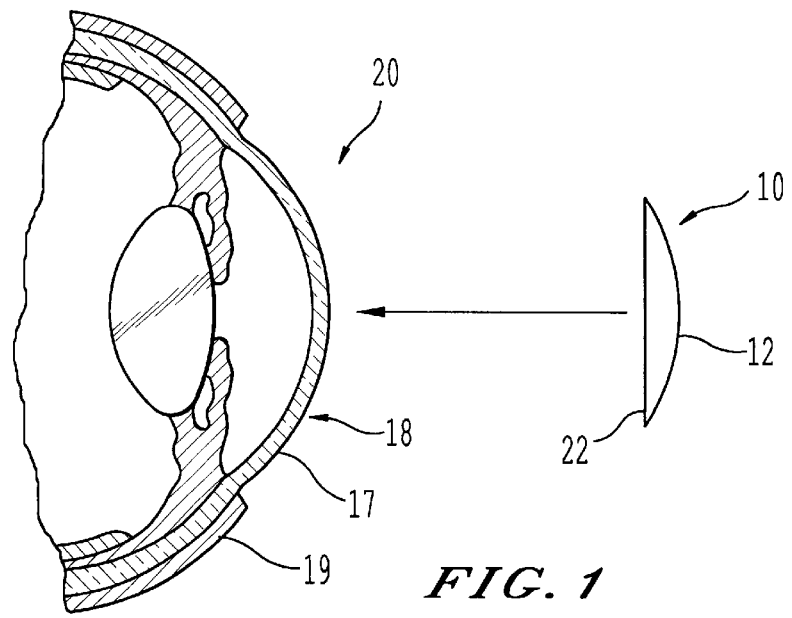
FIG. 1 is a cross-sectional view of an eye in relation to a contact lens according to an embodiment of the present invention positioned prior to placement on the eye.

FIGS. 1–4 illustrate a therapeutic contact lens 10 according to an embodiment of the present invention, which can have a size and overall shape similar to a conventional contact lens, or the lens can have a much larger diameter than a conventional contact. Lens 10 is formed having a first surface 12 and a second surface 14. The first and second surfaces 12 and 14 connect or define a portion or section 16 therebetween. First and second surfaces 12 and 14 and section 16 may be transparent or adapted to allow visible light to pass therethrough, and may include organic material or living cells.

The dimensions of the contact lens 10 have been exaggerated to more clearly show its interaction with the surface of the cornea 18 of 20 the eye.

Figure 2:
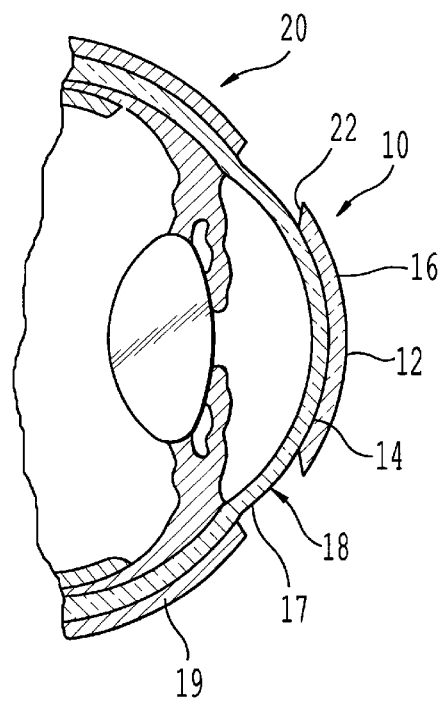
FIG. 2 is a cross-sectional view of the contact lens shown in FIG. 1 placed on the eye.
Figure 3:
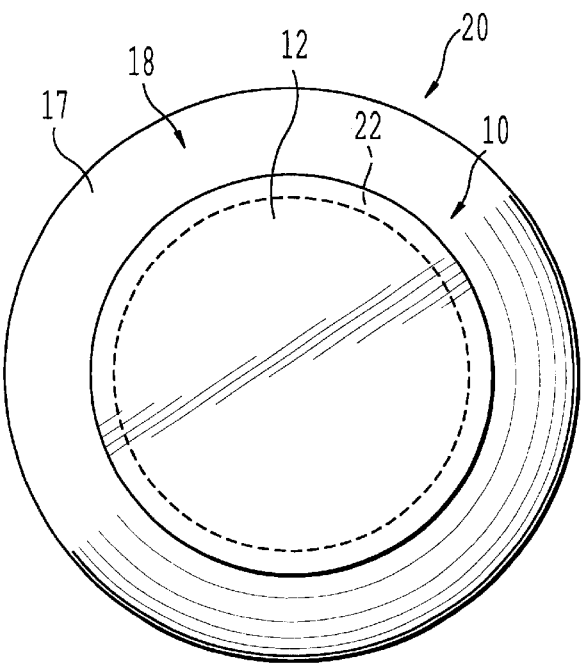
FIG. 3 is a front view of the contact lens shown in FIG. 1 placed on the eye.
Figure 4:
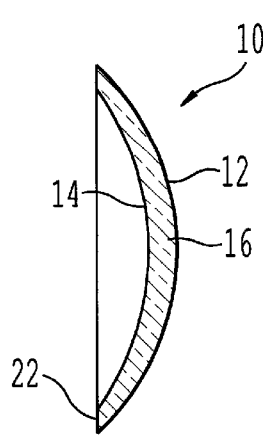
FIG. 4 is a detailed cross-sectional view of the contact lens shown in FIG. 1.

The first surface 12 is preferably a smooth or substantially smooth outer surface that is exposed to natural light or light outside the eye when the lens is positioned on the surface 17 of the cornea 18 of an eye 20. The lens may cover the both the cornea 18 and conjunctiva 19 of the eye or the cornea alone or the conjunctiva alone or any portion of either the conjunctiva and/or the cornea. As seen in FIGS. 2 and 4, in particular, the first surface 12 may have an arcuate shape that substantially follows the curvature of the cornea of the eye. Second surface 14 is preferably a smooth or substantially smooth inner surface that is substantially parallel or coplanar with first surface 12 and forms a similar arcute shape to surface 12, allowing surface 14 to be positioned adjacent to or flush with the cornea 18, as seen in FIG. 2. First and second surfaces 12 and 14 are separated by portion 16, as seen in FIGS. 2 and 4, with portion 16 terminating into edge or plane 22. Plane 22 extends about the perimeter of lens 10 as shown in FIG. 3.

It is noted that first and second surfaces 12 and 14 do not necessarily have to be arcute in shape, but may each be planar or substantially planar. In this event, lens 10 assumes a substantially similar shape of the cornea upon which it is positioned when the second surface 14 of the organic or living cell lens contacts and fits substantially flush with and adjacent to the cornea 18. The organic living cell material enables the lens 10 to be permeable and mold itself to the cornea 18 in a manner similar to that of existing soft contact lenses.

The surfaces 12 and 14 of the lens 10 may be shaped by any suitable shaping device or energy source, known to one of ordinary skill in the art. Preferably, either or both surfaces 12 and 14 are irradiated by an energy source, such as a laser or any other suitable energy source, which ablates a portion thereof and forms a refractive portion of the contact lens 10 as described in more detail below. The contact lens 10 may be cut or shaped prior to being positioned on the surface 17 of the cornea 18 or after being positioned on the surface of the cornea, as described in detail below. The shape, which each side may assume, is determined by the particular power and vision disorder of the eye 20. For example, an eye 20 may be near sighted, far sighted, or have astigmatism, and the appropriate type of lens having the appropriate curvature can be utilized to correct the particular vision problem. The present lens may be shaped in any manner suitable for correcting the vision of the wearer.

As discussed above, the lens 10 includes living cells. Preferably, substantially the entire lens 10 or portion 16 includes living cells. The living cells are preferably corneal cells that are initially grown in a culture having a nutrient rich medium. The culture is then shaped into the desired contact lens shape, as described above and in more detail below. The living cells are able to live for a predetermined period on the surface of the eye 20 by receiving nutrients that are provided by the tear field of the eye 20. The portion 16 is preferably formed by a protective film of five to six layers of cells in a litholyze state which include living stroma cells or a combination of stroma cells and epithelial cells. In addition, the living cells may include cells from the basement membrane and stormal cells. However, it is possible to form only a part or a percentage of the portion 16 from living cells, with the rest of the portion 16 being an artificial, synthetic or semisynthetic materiel, and the material and the living cells commingling during the culturing period. The artificial, semi-synthetic or synthetic materials may be biodegradable or permanent and replaced at a predetermined time by similar cells. A contact lens formed at least in part from living cells has an improved interaction with the cornea of the eye. In addition, the lens 10 may be soaked or coated with plasma or a serum mixture, prior to placement on the cornea or while positioned on the surface of the cornea 18. The serum mixture is preferably a 20 percent mixture of serum and a balanced salt solution that may have nutrients therein. The eye will have increased tolerance to a lens 10 coated in this manner, creating a more biocompatible lens than the prior art lenses.

The lens 10 may be disposable or left in the eye as long as the living cells are able to survive. Prior to use, the lens 10 can be stored in a saline solution having nutrients, such as glucose, or the like. The lens 10 may also be shipped in a frozen state or dry frozen, or in any other state that preserves the structure of the cells. It is not necessary that all of the cells be living upon use. Although, some cells may die during use, these dead cells will not effect the characteristics or performance of the lens 10.

The therapeutic contact lens 10 may also be utilized as a bandage. The lens 10 may have no refractive power or any desired refractive power when used as a bandage, as long as the lens 10 covers the area of interest of the cornea 18. For protective purposes, the lens 10 is sized accordingly (large, small, refractive, nonrefractive) and placed on the cornea 18 of the eye 20 to cover an abrasion, infection, ulcer or an incision, such as an incision made during the Lasik procedure. In addition, lens 10 may be used to cover trauma to the eye where a portion of the cornea or epithelia is damaged or where a portion of the cornea or epithelia is removed during a surgical procedure, such as photo refractive kratectomy. A lens 10 used in this manner would not only facilitate or promote the healing process, but would also protect the eye from outside materials, such as dust, dirt and the like. In addition, the lens may be soaked in antibiotics or the first and/or second surfaces 12 and 14 of the lens may be coated with antibiotics or any other suitable material for healing or protective purposes. The antibiotics may be adapted for slow release into the eye 20 and for soothing the eye 20 and facilitating the healing process over an extended period of time. Additionally, the lens 10 could provide antifungal or anti-inflammatory measures and may provide relief from dry eye syndrome by having an immunomodulator, such as, cycosporin A or Tacrolimus applied to it.

Figure 5:
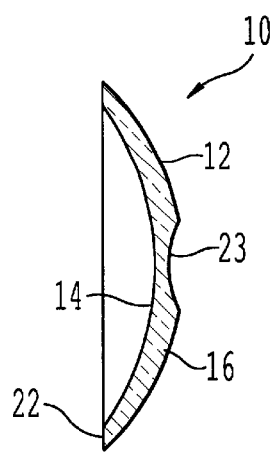
FIG. 5 is a detailed cross-sectional view of a contact lens with a second surface having a concave shape according to another embodiment of the present invention.
Figure 6:
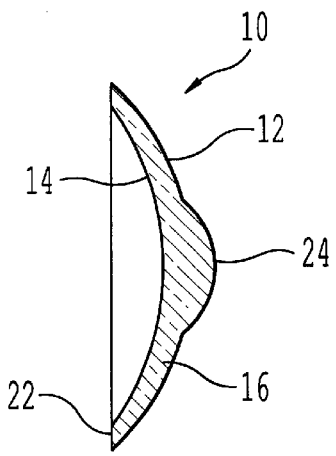
FIG. 6 is a cross-sectional view of a contact lens with a second surface having a convex shape according to a further embodiment of the present invention.
Figure 7:
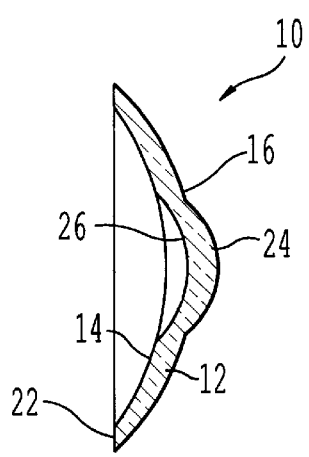
FIG. 7 is a cross-sectional view of a contact lens with a first surface having a concave shape and a second surface having a convex shape according to a further embodiment of the present invention.
Figure 8:
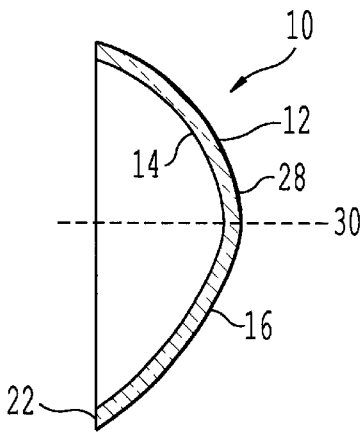
FIG. 8 is cross-sectional view of a contact lens having an asymmetrical shape for correcting an astigmatism according to a further embodiment of the present invention.
Figure 9:
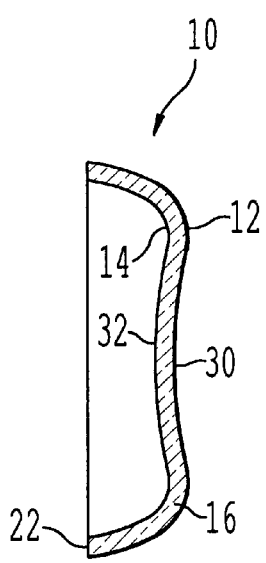
FIG. 9 is cross-sectional view of a contact lens with a first surface having a convex shape and a second surface having a concave shape according to a further embodiment of the present invention.

Additionally first and second surfaces 12 and 14 do not necessarily have to be substantially parallel. As shown in FIGS. 5–9, first and second surfaces 12 and 14 may each be convex, concave and/or asymmetrical, or any other suitable shape. As seen in FIG. 5, first surface 12 may have a concave portion 23 to correct a vision disorder, such as myopia. As seen in FIGS. 6 and 7, first surface 12 may have a convex portion 24 and second surface 14 may not have any change in its surface. Alternatively, second surface 14 may have a concave portion 26, as seen in FIG. 7. Lens 10 may be asymmetrical, wherein the apex 28 of the lens is off-center from the centerline 30 of the lens 10, as shown in FIG. 9. Additionally, the lens 10 may have a concave portion 30 and convex portion 32, with the first and second surfaces 12 and 14 remaining substantially parallel to each other for the entire length of the lens. It is noted that these confirmations are not meant to limit the present invention, but are only shown as examples of possible combinations of refractive properties of a lens 10. Each surface of the lens 10 may have any or no refractive, depending on a specific property necessary to correct a specific vision problem.

Figure 10:
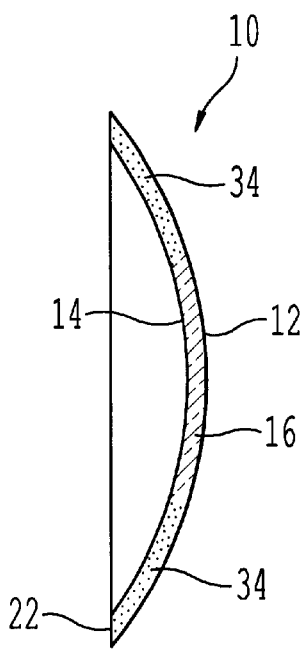
FIG. 10 is a cross-sectional view of a contact lens with a transparent portion having pigmentation according to a further embodiment of the present invention.
Figure 11:
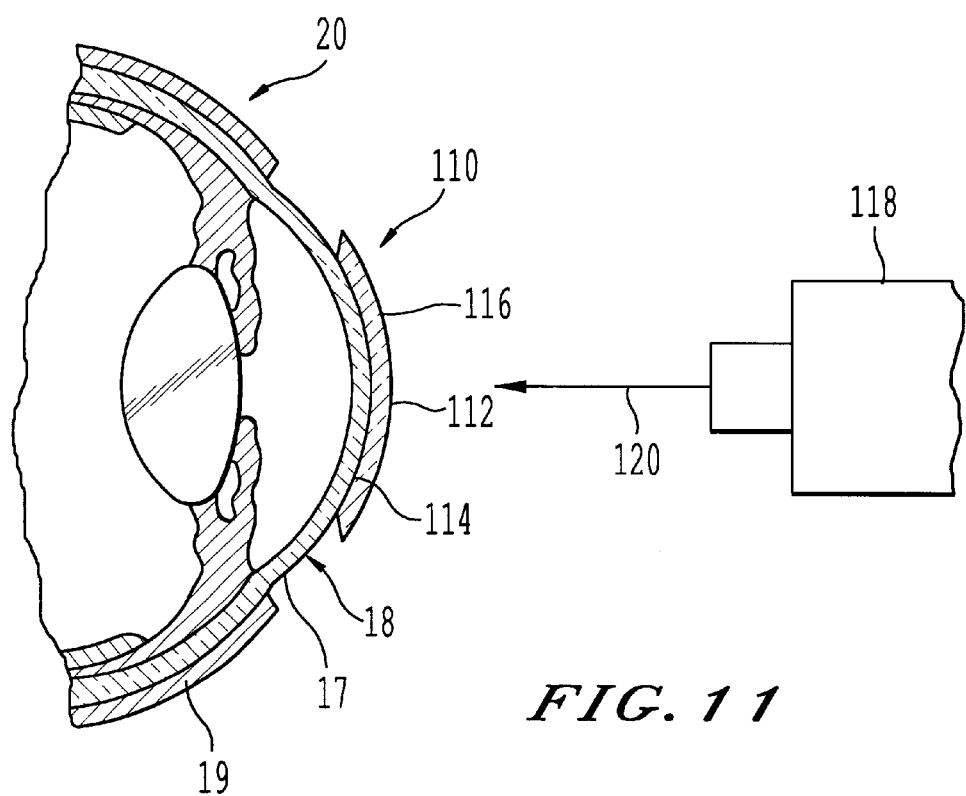
FIG. 11 is a cross-sectional view of an eye having a contact lens thereon which can be shaped with energy irradiated from an energy source according to another embodiment of the present invention.

Portion 16 and/or surfaces 12 and 14 may also have pigmentation 34 on or at the perimeter of the lens, as shown in FIG. 10, for changing the color of the iris, aniridic eyes (eyes having no iris), or eyes suffering from trauma wherein all or a portion of the iris has been removed. The pigmentation 34 may be placed on the first surface 12 and/or the second surface 14, or it may be incorporated into portion 16. The pigmentation 34 is preferably located at the perimeter of the lens, but may cover the entire surface of either or both surfaces 12 and 14 and/or be incorporated throughout the entire portion 16 or any part of the portion 16. Furthermore, the pigmentation 34 may be any suitable color and/or any material for protection against ultra-violet radiation. For example, carbon particle or any standard coloring.

Method of Manufacturing Lens—FIGS. 11–14

As shown in FIGS. 11–14, a method for manufacturing a contact lens 110 according to an embodiment of the present invention may result in the contact lens 110 that is similar to contact lens 10 described above. Lens 110 is formed having a first surface 112 and a second surface 114, which define a portion or section 116 therebetween, which have characteristics similar to first and second surfaces 12 and 14 described above. First and second surfaces 112 and 114 and section 116 may be transparent or adapted to allow visible light to pass therethrough. Lens 110 may be formed from living cells, a matrix or hybrid of living cells and artificial, synthetic or semi-synthetic material commingling during the culture process, as described above, or any other suitable material or substance. Preferably, the lens is a soft contact lens, a lens having a high water content, or a living cell lens 10 as described above. These types of lenses are preferred due to the fact that hard contacts must have accurate measurements to contact the cornea, and generally do not sit properly on the surface of the cornea for laser ablation purposes.

According to the method, a nonrefractive lens 110 as described above is placed on the cornea 18 of an eye 20. Using existing wavefront technology, as is known to one skilled in the art, the refractive power of the eye may then be precisely measured. This information is then downloaded into a system that, using current technology, determines a pattern that energy emitting source 118 (preferably an excimer laser) is to form by irradiating the first surface 112 of the lens and ablating a three dimensional section of the portion 116 corresponding to the pattern. The energy source 118 is then directed at the lens 110 and emits a beam of radiant energy 120 to irradiate and thus ablate a three dimensional portion of the section 116. However, the contact lens may be shaped by any suitable shaping device or energy source, such as infrared light, which would cause the lens to shrink, or a fiber optic probe either to touch the contact lens and ablate a portion thereof or to irradiate with energy from a suitable distance.

Figure 12:
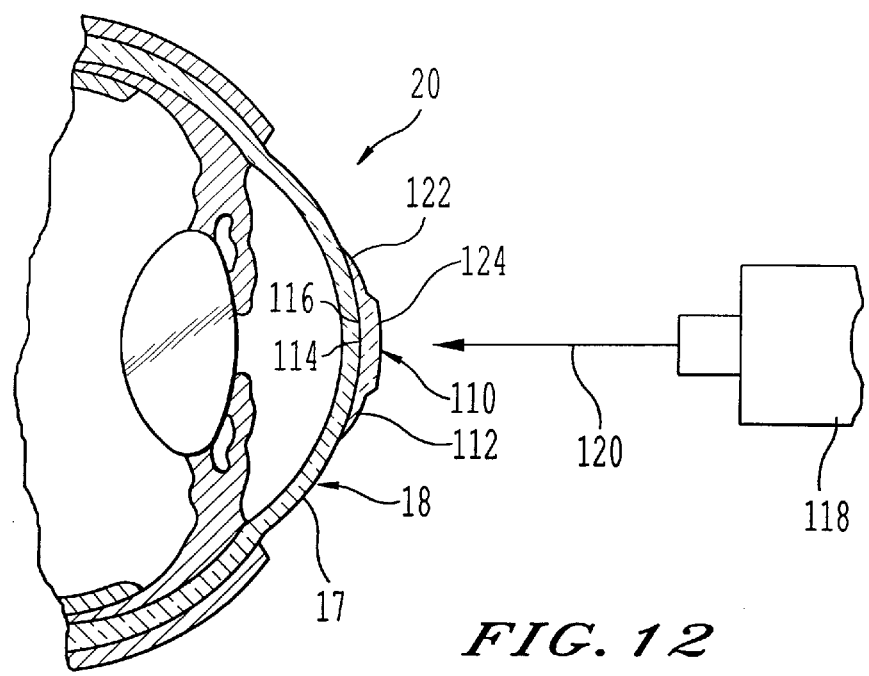
FIG. 12 is a cross-sectional view of a contact lens shown in FIG. 11 after irradiation from the energy source, with a section of the transparent portion ablated to form a convex lens.
Figure 13:
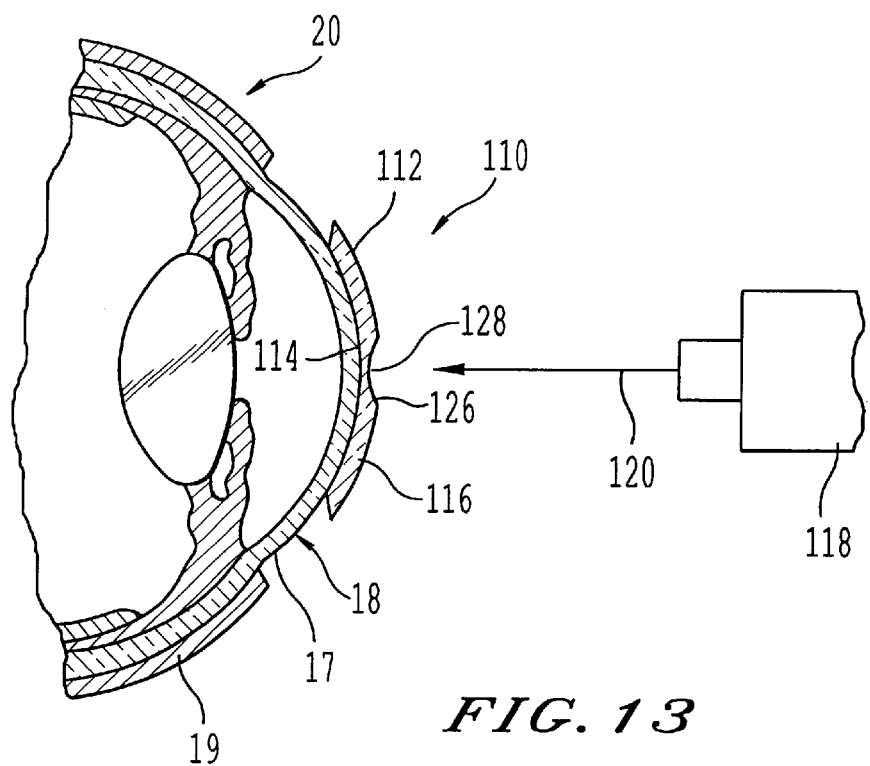
FIG. 13 is a cross-sectional view of a contact lens shown in FIG. 11 after irradiation from the energy source, with a section of the transparent portion ablated to form a concave lens.
Figure 14:
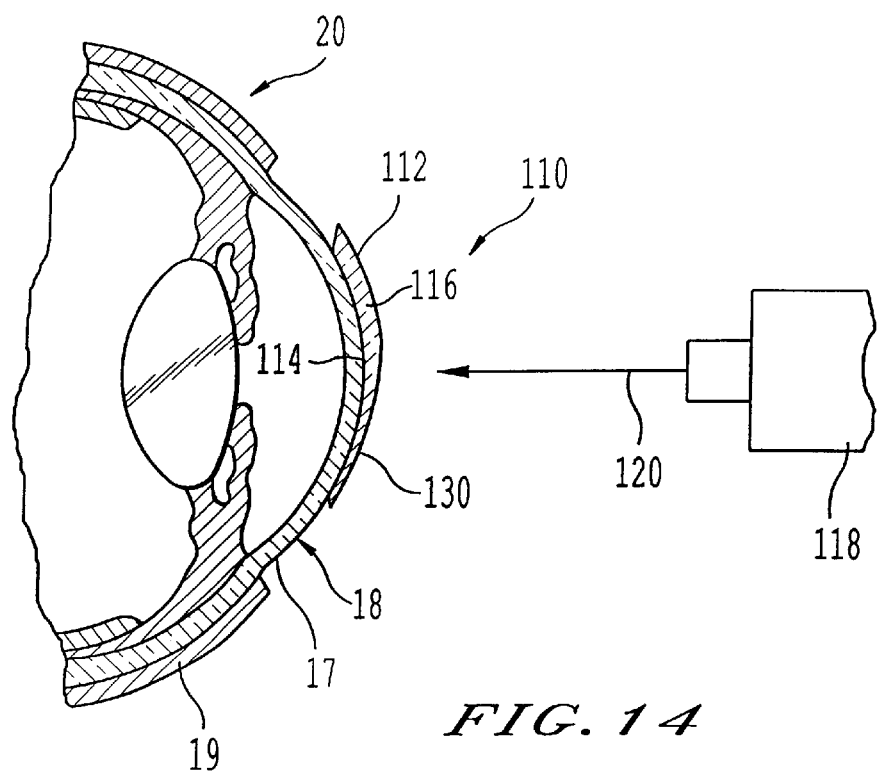
FIG. 14 is a cross-sectional view of a contact lens shown in FIG. 11 after irradiation from the energy source, with a section of the transparent portion ablated to form a lens for correcting astigmatism.

The ablation of the contact lens 110 results in a removable lens that is specifically measured and shaped for an individual and is a custom or personal contact lens with substantially perfect corrective properties. By ablating lens 110 using an energy source in this manner, many types of vision problem may be corrected. As shown in FIGS. 12–14, the resulting lens may be concave, convex, or asymmetrical for correcting near and far sighted vision, and astigmatism. FIG. 12 specifically shows a portion 122 of lens 110 ablated, forming a convex portion 124 on the first surface 114 of lens 110. Similarly, FIG. 13 shows a portion 126 of lens 110 ablated, forming a concave portion 128 on the first surface 112 of lens 110. Additionally, FIG. 14 shows a portion 130 that forms an asymmetrical lens 110 for correcting astigmatism. These embodiments are not meant to limit the present invention to only these embodiments, and are only shown as examples of possible combinations of refractive properties of a lens.

Figure 15:
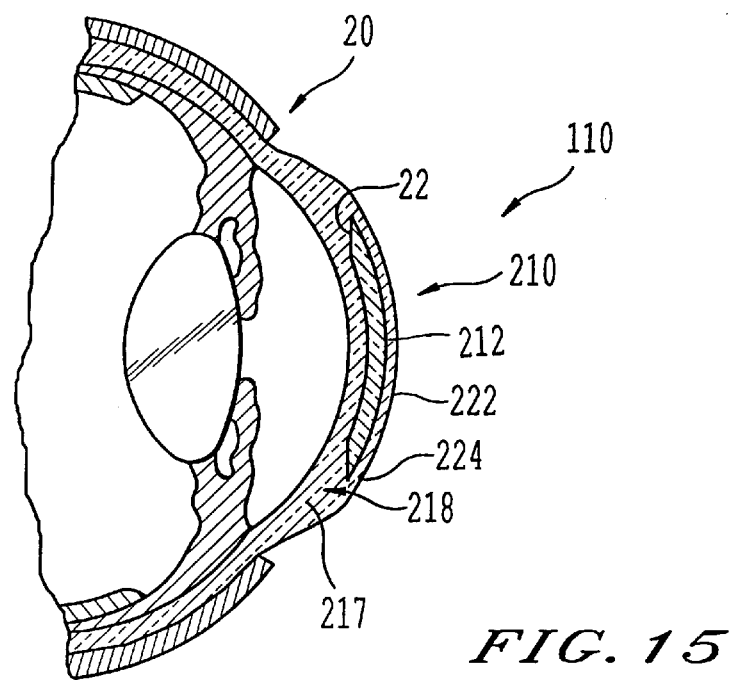
FIG. 15 is a cross-sectional view of an eye in relation to a lens according to a further embodiment of the present invention positioned prior to placement on the eye.

Embodiment of FIG. 15

As seen in FIG. 15, a living cell lens 210 may be positioned on the surface 217 of the cornea 218 of an eye 220. As described above the cornea may be damaged due to trauma or may have undergone a surgical procedure in which a portion of the epithelia is removed. A damaged epithelia may also have a portion surgically removed to make the surface even, allowing a better fit between the lens 210 and the cornea 218.

The lens 210 is preferable formed from living cells as described above, but may be formed partially from any suitable artificial, semi-synthetic or synthetic material forming a matrix or hybrid with the living cells, as described above. Additionally, lens 210 may be attached to the cornea using any suitable method such as, a bioadhesive. By attaching the lens with a bioadhesive, it permits the corneal epithelial 222 to grow over then lens 210, forming a permanent living cell lens, as shown in FIG. 15. Preferably the epithelial may grow over the entire surface 212 of lens 210 or it may only grow over the perimeter 224 of the lens.

The lens may have no refractive power or have any suitable refractive power necessary to alter light passing through the lens and correcting for any suitable vision disorder such as myopia, hyperopia, and/or astigmatism, as described above.

While a few specific embodiments have been chosen to illustrate the invention, it will be understood by those skilled in the art that various changes and modifications can be made therein without departing from the scope of the invention as defined in the appended claims.

What is claimed is:

1. A lens for removable placement onto a surface of at least one of a cornea and a conjunctiva tissue of an eye, comprising:
   a first surface adapted for exposure to light; and
   a second surface adapted to contact said surface of the cornea;
   said first and second surfaces defining a portion therebetween including living cells and artificial material, said artificial material and said living cells being commingled in a matrix in said portion, said portion being adapted to allow visible light to pass therethrough.

2. A lens according to claim 1, wherein:
   said living cells include corneal cells.

3. A lens according to claim 1, wherein:
   at least one of said first and second surfaces is coated with an antibiotic.

4. A lens according to claim 1, wherein:
   said portion includes a refractive portion adapted to refract said visible light passing therethrough.

5. A lens for removable placement onto a surface of at least one of a cornea and a conjunctiva tissue of an eye, comprising:
   a first surface adapted for exposure to light; and
   a second surface adapted to contact said surface of the cornea;
   said first and second surfaces defining a portion therebetween including living cells and artificial material, said artificial material and said living cells being commingled in a matrix in said portion, said portion being adapted to allow visible light to pass therethrough and to absorb energy irradiating onto at least one of said first and second surfaces so that said energy can ablate a section of said portion to form a refractive portion.

6. A lens according to claim 5, wherein:
   said portion is adapted to absorb said energy while said second surface is in contact with said surface of said cornea.

7. A lens according to claim 5, wherein:
   said energy includes laser light.

8. A lens according to claim 5, wherein:
   said portion includes pigmentation disposed therein.

9. A lens according to claim 5, wherein:
   said portion includes ultraviolet light absorbing-material disposed therein.

10. A lens according to claim 5, wherein:
    at least one of said first and second surfaces is coated with an antibiotic.

11. A lens according to claim 5, wherein:
    said living cells include stromal cells.

12. A lens according to claim 4, wherein:
    said portion is adapted to absorb energy irradiating onto at least one of said first and second surfaces so that said energy can ablate a section of said portion to form the refractive portion.

13. A lens according to claim wherein:
    said portion is adapted to absorb said energy while said second surface is in contact with said surface of said cornea.

14. A lens according to claim 12, wherein:
    said energy includes laser light.

15. A lens according to claim 1, wherein:
    said portion includes pigmentation disposed therein.

16. A lens according to claim 1, wherein:
    said portion includes ultraviolet light absorbing material disposed therein.

17. A lens according to claim 12, wherein:
    said living cells include stromal cells.

18. A lens for removable placement onto a surface of at least one of a cornea and a conjunctiva tissue of an eye, comprising:
    a first surface adapted for exposure to light; and
    a second surface adapted to contact said surface of the cornea;
    said first and second surfaces defining a portion therebetween including living cells and artificial material, said artificial material and said living cells being commingled in a matrix in said portion, said portion being adapted to absorb energy irradiating onto at least one of said first and second surfaces so that said energy can ablate a section of said portion to form a refractive portion.

19. A lens according to claim 18, wherein:
    said portion is adapted to absorb said energy while said second surface is in contact with said surface of said cornea.

20. A lens according to claim 18, wherein:
said energy includes laser light.

21. A lens according to claim 18, wherein:
at least one of said first and second surfaces is coated with an antibiotic.

22. A lens according to claim 18, wherein:
said portion includes pigmentation disposed therein.

23. A lens according to claim 18, wherein:
said portion includes ultraviolet light absorbing material disposed therein.

24. A lens according to claim 18, wherein:
said living cells include stromal cells.

* * * * *